United States Patent [19]

Forman et al.

[11] Patent Number: 5,206,222
[45] Date of Patent: Apr. 27, 1993

[54] METHODS FOR THE REDUCTION OF MYOCARDIAL REPERFUSION INJURY

[75] Inventors: Mervyn B. Forman, Nashville, Tenn.; Edwin K. Jackson, Pittsburg, Pa.

[73] Assignee: Vanderbilt University, Nashville, Tenn.

[21] Appl. No.: 704,058

[22] Filed: May 22, 1991

[51] Int. Cl.$^5$ .................... C07H 19/067; A61K 31/70
[52] U.S. Cl. ..................................... 514/46; 514/564; 536/27.22
[58] Field of Search ............................ 536/26; 514/46

[56] References Cited

U.S. PATENT DOCUMENTS

| 4,985,409 | 1/1991 | Yamada et al. | 514/46 |
| 5,023,244 | 6/1991 | Goto et al. | 514/46 |

FOREIGN PATENT DOCUMENTS

| 0263071 | 4/1981 | European Pat. Off. |
| 0267878 | 11/1986 | European Pat. Off. |
| 0323807 | 7/1989 | European Pat. Off. |
| 0354180 | 2/1990 | European Pat. Off. |

OTHER PUBLICATIONS

Takeo et al., J. Pharmacol. Exp. Therapeutics, 248(1), 306–314 (1989).
Takeda et al., Shinshu Igaku Zasshi, 36(1), 55–72 (1988); Chem. Abstr., 109, p. 40 (1988), Abstr. No. 3179n; Only Abstract supplied.
Honig et al., Adv. Exp. Med. Biol., 75, 623–630 (1976); Chem. Abstr., 90(21), Abstr. no. 165,756x(1976); Only Abstract supplied.
Amrosio et al., Progressive Impairment of Regional Myocardial Perfusion After Initial Restoration of Postischemic Blood Flow, Circulation 80:1846–1861 (1989).
Abd-Elfattah et al., Myocardial Reperfusion Injury: Role of Myocardial Hypoxanthine and Xanthine in Free Radical-Mediated Reperfusion Injury, Circulation 78: III224–235 (1988).
Babbitt et al., Intracoronary Adenosine Administered After Reperfusion Limits Vascular Injury After Prolonged Ischemia in the Canine Model, Circulation, 80:1388–1399 (1989).
Bajaj et al., Limitation of Myocardial Reperfusion Injury by Intravenous Perfluorochemicals, Circulation 79:645–656 (1989).
Belardinelli et al., Chronotropic and Dromotropic Effects of Adenosine. In Regulatory Function of Adenosine. ed. R. M. Berne, T. W. Rall, Rubio. Boston, Martinus/Nijoff, pp. 337–398 (1983).
Berne, The Role of Adenosine in the Regulation of Coronary Blood Flow, Cir. Res. 47:807–813 (1980).
Biaggioni et al., Cardiovascular and Respiratory Effects of Adenosine in Conscious Man Evident for Chemoreceptr Activation, Cir. Res. 61: 779–786 (1987).
Brodeur, Effects of Adenosine on Functional Recovery During Reperfusion of the Ischemic Rabbit Myocardium, ABstract Scientific Session III-289 (1990).
Carlsson et al., Local Release of Myocardial Norepinesphrine During Acute Ischemia: An Experimental Study in the Isolated Perfused Rat Heart. J. Cardiovasc. Pharmacol. 7:791–798 (1985).
Clemo et al., Effect of Adenosine on Atrioventricular Conduction. I: Site and Characterization of Adenosine Action in the Guinea Pig Atrioventricular Node, Cir. Res. 59:427–436 (1986).

(List continued on next page.)

Primary Examiner—Johnnie R. Brown
Assistant Examiner—L. Eric Crane
Attorney, Agent, or Firm—Tilton, Fallon, Lungmus & Chestnut

[57] ABSTRACT

This invention relates to a method to treat a heart attack victim to reduce heart muscle damage. In particular, the invention relates to a method to reduce myocardial reperfusion injury by selectively administering a non-hypotensive amount of a compound that selectively activates adenosine-1 receptor, a compound that selectively activates adenosine-2 receptor, or a adenosine, all in the presence of an effective amount of lidocaine.

8 Claims, 1 Drawing Sheet

OTHER PUBLICATIONS

Cronstein et al., Adenosine: A Physiological Modulator of Superoxide Anion Generation by Human Neutrophils, J. Exp. Med, 158: 1160–1177 (1983).

Cronstein et al., Adenosine: An Endogenous Inhibitor of Neutrophil-mediated Injury to Endothelial Cells, J. Clin. Invest. 78: 760–770 (1986).

Daval et al., Protective Effect of Cyclohexyl-adenosine on Adenosine $A_1$ Receptors, Guanine Nucleotide and Forskolin Binding Sites Following Transient Brain Ischemia: A Quantitative Autoradiographic Study, Brain Res. 491:212–226 (1989).

Dobson et al., The Cardiac Anti-Adrenergic Effect of Adenosine, Progress in Clinical an Biologic Research, 230:331–343 (1987).

Ely et al., Functional and Metabolic Evidence of Enhanced Myocardial Tolerance to Ischemia and Reperfusion with Adenosine, J. Thorac. Cardiovasc. Surg. 90:549–556 (1985).

Engler et al., Leukocyte Capillary Plugging in Myocardial Ischemia and Reperfusion in the Dog, Am. J. Pathol. 111:98–111 (1983).

Evans et al., Adenosine Receptors Mediating Cardiac Depression, Life Sciences, 31:2425–2432 (1982).

Fantone et al., Polymorphonuclear Leukocyte-mediated Cell and Tissue Injury: Oxygen Metabolites and Their Relation to Human Disease, Human Pathol. 16:973–978 (1985).

Forman et al., Mechanism and Therapy of Myocardial Reperfusion Injury, Circulation 81: IV69–IV78 (1990).

Forman et al., Preservation of Endothelial Cell Structure and Function by Intracoronary perfluorochemical in a Canine Preparation of Reperfusion. Circulation 76:469–479 (1987).

Maneda et al., Effects of Nicorandil and Nipradilol on Ischemic Myocardium in Perfused Rat Heart, European J. of Phamocol. 162:81–87 (1989).

Homeister et al., Combined Adenosine and Lidocaine Administration Limits Myocardial Reperfusion Injury, Circulation 82:595–607 (1990).

Hori et al. (I), Adenosine-induced Hyperemia Attenuates Myocardial Ischemia in Coronary Microembolization in Dogs, Am. Physiol., H244–H250 (1989).

Hori et al. (II), AICA-riboside (5-amino-4-imidazoic carboxamide riboside 100), a Novel Adenosine Potentiator, Attenuates, Myocardial Stunning, Circulation, 82:III-466 (1990).

Hutchinson et al., CGS 21680C, An $A_2$ Selective Adenosine Receptor Agonist with Preferential Hypotensive Activity, J. Pharm. & Exp. Thera. 251: 47–55 (1989).

Kitakaze et al., Stimulations of Adenosine $A_1$ and $A_2$ Receptors Prevent Myocardial Stunning, Scientific Sessions, III–37 (1990).

Kitakaze et al., Endogenous Adenosine Inhibits Formation of Microthomboembolism in Ischemic Myocardium, Circulaton 82:III-276 (1990).

Koke et al., Inhibitors of Adenosine Catabolism Improve Recovery of Dog Myocardium After Ischemia, J. Molecular & Cellular Biochemistry 86:107–113 (1989).

Kuroda, Modulation of Calcium Channels Through Different Adenosine Receptors; ADO-1 and ADO-2, Adenosine: Receptors and Modulation of Cell Function, Eds. V. Stafanovich, K. Rudlophi and P. Schubert. IRL Press Limited, Oxford, England, pp. 233–239 (1985).

Ledingham et al., Beneficial Effect of Adenosine During Reperfusion Following Prolonged Cardioplegic Arrest, Cardivascu. Res. 24:247–253 (1990).

Lohse et al., 2-Chloro-$N^0$-cyclopenthyladenosine: A Highly Selective Agonist at $A_1$ Adenosine Receptors, Naunyn-Schmiedeberg's Arch. Pharamcol. 337:687–689 (1988).

Olafsson et al., Reduction of Reperfusion Injury in the Canine Preparation by Intracoronary Adenosine: Importance of the Endothelium and the No-Reflow Phenomenon, Circulation, 6:1135–1141 (1987).

Pitarys et al., Reduction of Myocardial Reperfusion Injury by Intravenous Adenosine Administered During the Early Reperfusion Period, Circulation 83:237–247 (1991).

Richardt et al., Adenosine Inhibits Exocytotic Release of Endogenous Noradrenalin in Rat Heart: A Protective Mechanism in Early Myocardial Ischemia, Circ. Res. 61:117–123 (1987).

Rousseau et al., Is It Worth Increasing Myocardial Adenosine During Reperfusion? A Pilot Trial of Combined rt-PA and Dipyridamole Infusion, Circulation 82:IV-666 (1990).

(List continued on next page.)

OTHER PUBLICATIONS

Stiles, Adenosine Receptors and Beyond: Molecular Mechanisms of Physiological Regulation, Clin. Res., 38:10–18 (1990).

Tanabe et al., Inhibition of Coronary Circulatory Failure and Thromboxane $A_2$ Release During Coronary Occlusion and Reperfusion by 2-phenylamino-adenosine (CV-1808) in Anesthetized Dogs, J. Cardiovasc. Pharmacol. 6:442–448 (1984).

Angello et al., Adenosine Antagonism Decreases Metabolic But Not Functional Recovery From Ischemia, Am. Physiol., H193–H199 (1991).

Thornton et al., Preconditioning Protection is Mediated Through Adenosine Receptors, Circulation 82:III–464 (1990).

Weihprecht et al., Effect of Adenosine $_1$ Receptor Blockade on Renin Release from Rabbit Isolated Perfused Juxtaglomerular Apparatus, J. Clin. Invest 85:1622–1628 (1990).

Wyatt et al., Adenosne Stimulated Glycolytic Flux in Isolated Perfused Rat Hearts by $A_1$-Adenosine Receptors, Am. J. Physiol. 257:H1952–H1957 (1989).

Zhu et al., Protective Effects of an Adenosine Deaminase Inhibitor on Ischemia-Reperfusion Injury in Isolated Perfused Rat Heart, Am. J. of Physo. 259:H835–H838 (1990).

Fig. 1

METHODS FOR THE REDUCTION OF MYOCARDIAL REPERFUSION INJURY

Grant Statement

This research was supported in part by the National Institute of Health, Grant R01 HL40892-01.

Background of the Invention

1. Field of the Invention

This invention relates to a method to treat a heart attack victim to reduce heart muscle damage. In particular, the invention relates to a method to reduce myocardial reperfusion injury by administering adenosine in such a low dose that it does not produce negative side-effects. Additionally, this invention relates to a method to reduce myocardial reperfusion injury by administering compounds that activate adenosine receptor sites.

2. Background of the Invention

Approximately 1.5 million Americans suffer a heart attack each year. Both the short and long term survival in these patients is dependent on the amount of heart muscle damage. The introduction of potent thrombolytic (clot dissolving) drugs and balloon angioplasty has resulted in reperfusion as a logical treatment for patients with an acute heart attack. However, the introduction of oxygen and white blood cells into the heart muscle when the clot dissolves is associated with additional damage to the small blood vessels downstream from the main arteries. This results in an increase in the amount of heart muscle damaged ("reperfusion injury"). Administration of drugs that prevent this occurrence could result in a substantial saving of heart muscle and improvement of the pumping function of the heart.

Adenosine is an endogenous arteriolar vasodilator present in relatively high concentrations at the time of reperfusion. Berne, Cir. Res., 47:807 (1980) Adenosine is a metabolic by-product of ATP and it has certain cardioprotective effects that may attenuate reperfusion injury.

It has been shown that the administration of adenosine after reperfusion limits vascular injury after prolonged ischemia. Babbitt et al., Circulation, 80:1388 (1989); Olaffson et al., Circulation, 76:1135 (1987); Forman et al., Circulation, 81:IV-69 (1990); Pitarys et al., Circulation, 83:237 (1991). When adenosine is infused into humans, however, it causes anxiety, increases heart rate, produces a feeling of pressure on the chest, and causes a general feeling of extreme discomfort. These negative effects mitigate against using adenosine to treat a heart attack victim.

SUMMARY OF THE INVENTION

The present invention relates to a method to reduce myocardial reperfusion injury by administering a non-hypotensive dose of adenosine. Surprisingly such a low dose of adenosine, still reduces myocardial reperfusion injury without causing negative side-effects.

Additionally, this invention relates to a method to reduce myocardial reperfusion injury by administering compound that activate adenosine receptor sites.

In particular, this invention relates to a method to reduce myocardial reperfusion injury by administering a compound that selectively activates adenosine-1 receptor or adenosine-2 receptor. These compounds are administered in such low doses that they do not cause the negative side effects previously associated with adenosine administration.

Still another advantage of this invention is to administer adenosine or compounds that activate adenosine receptor sites intravenously to reduce reperfusion associated tissue damage.

DETAILED DESCRIPTION OF THE INVENTION

Reperfusion injury is the limiting factor that determines to what extent a patient will recover from a heart attack. The present method has been shown to reduce myocardial reperfusion injury in rabbits. Rabbit hearts are a good model for extrapolating to the human heart. Rousseau, et al. Circulation 82:2646 (1990).

As previously stated, this invention relates to the discovery that myocardial reperfusion injury can be reduced by administering an nonhypotensive amount of 1) a compound that selectively activates the adenosine-1 receptor; 2) a compound that selectively activates the adenosine-2 receptor, or 3) adenosine itself. It should also be noted that the coadministration of lidocaine may be necessary for beneficial results.

The endogenous compound adenosine plays a role in limiting myocardial ischemia reperfusion injury through its ability to cause vasodilation, modulate cardiac adrenergic responses, inhibit neutrophil function, or modulate energy supply and demand for the myocardium Homeister et al, Combined Adenosine and Lidocaine Administration Limits Myocardial Reperfusion Injury, Circulation, 82:595-08 (1990).

Similarly, the stimulation of the adenosine-1 receptor results in various metabolic effects which may prove to be beneficial. Firstly, myocardial ischemia is associated with an increase in endogenous catecholamines which would increase myocardial energy utilization through stimulation of beta-adrenoreceptors. Carlsson L., Abrahamsson T., Almgren O.: Local Release of Noradrenaline During Acute Ischemia. An Experimental Study in the Isolated Perfused Rat Heart. J. Cardiovasc. Pharmacol. 7:791-8 (1985). Adenosine has been shown to reduce norepinephrine release from sympathetic nerve endings primarily through its action on the adenosine-1 receptor. Richardt, G., Waas, W., Kronzhomig, R., Mayer, E., Schomig, A.: Adenosine Inhibits Exocytotic Release of Endogenous Noradrenalin in Rat Heart: A Protective Mechanism in Early Myocardial Ischemia. Circ. Res. 61:117-23 (1987). Secondly, adenosine can increase glucose influx in the globally hypoxic heart through activation of the adenosine-1 receptor. Wyatt, D. A., Edmunds, M. C., Rubio, R., Berne, R. M., Lasley, R. D., Mentzer, R., Jr.: Adenosine Stimulates Glycolytic Flux in Isolated Perfused Rat Hearts by $A_1$-Adenosine Receptors. Am. J. Physiol. 257:H1952-7 (1989). Thirdly, both the chronotropic and dromotropic effects of adenosine-1 stimulation on the conducting system would result in a decrease in a myocardial oxygen consumption. Belardinelli, L., West, A., Crampton, R., Berne, R.M.: Chronotropic and Dromotropic Effects of Adenosine. In Regulatory Function of Adenosine. ed. R. M. Berne, T. W. Rall, R. Rubio. Boston, Martinus/Nijoff, pp. 337-96 (1983). Therefore, the effects of adenosine in myocardial reperfusion injury may be secondary to an improvement in the metabolic substrate of the reperfused myocardium.

Myocardial ischemia is associated with a progressive increase in cytosolic calcium. Steenberger, C., Murphy, E., Levy, L., London, R. E.: Elevation in Cytosolic Free Calcium Concentration Early in Myocardial Ischemia in Perfused Rat Heart. Circ. Res. 60:700–7 (1987). Marban, E. Kitakze, M., Kusuokw, H., Porterfield, J. K., Yuo, D. T., Chacko, V. P.: Intracellular Free Calcium Concentration Measured with $^9$F NMR Spectroscopy in Intact Ferret Hearts. Proc. Nat'l. Acad. Sci. USA 86:6005–9 (1987). Stimulation of adenosine-1 receptors could reduce calcium overload during reperfusion either by inhibiting potassium dependant calcium uptake from viable cells or by impeding further calcium uptake through blockade of calcium dependent channels. Kuroda, Y.: Modulation of Calcium Channels Through Different Adenosine Receptors; ADO-1 and ADO-2. In *Adenosine: Receptors and Modulation of Cell Function*. Eds. V. Stafanovich, K. Rudlophi and P. Schubert. IRL Press Limited, Oxford, England, pp. 233–9 (1985). Schubert, P.: Synaptic and Non-synaptic Modulation by Adenosine: a Differential Action of K- and Ca- Fluxes. In *Adenosine: Receptor and Modulation of Cell Function*. Eds. V. Stefanovich, K. Rudlophi, and P. Schubert. IRL Press Limited, Oxford, England, pp. 117–29 (1985).

The role of oxygen derived free radicals in the pathogenesis of reperfusion injury remains controversial and this subject has been reviewed recently by Engler and Gilpin. Carlsson, L., Abrahamsson, T., Almgren, O.: Local Release of Noradrenaline During Acute Ischemia. An Experimental Study in the Isolated Perfused Rat Heart. J. Cardiovasc. Pharmacol. 7:791–8 (1985). Stimulation of the adenosine-1 receptor could, theoretically, decrease free radical formation following reperfusion by reducing lipolysis, and therefore inhibiting the formation of lipid hydroperoxides, and by decreasing the quantity of catecholamines available for auto-peroxidation.

Additionally, it was discovered that compounds that selectively activate adenosine-2 receptors reduce myocardial reperfusion injury. The current understanding of the pathogenesis of myocardial reperfusion injury suggests that activation of the adenosine-2 receptor would be the most likely mechanism to account for the protective effects of adenosine. Previous studies have shown that reperfusion produces structural and functional abnormalities in both the large and small blood vessels resulting in a progressively decreasing blood flow during the peri-reperfusion period. Forman, M. B., Puett, D. W., Binham, S. E., Virmani, R., Tantengco, M. V., Light, R. T., Bajaj, A. K., Price, R., Friesinger, G. C.: Preservation of Endothelial Cell Structure and Function by Intracoronary Perfluorochemical in a Canine Preparation of Reperfusion. Circulation 76:469–79 (1987). Babbitt, D. G., Virmani, R., Forman, M. B.: Intracoronary Adenosine Administered After Reperfusion Limits Vascular Injury After Prolonged Ischemia in the Canine Model. Circulation 80:1388–99 (1989). Ambrosio, G., Weisman, H. F., Mannisi, J. A., Becker, L. C.: Progressive Impairment of Regional Myocardial Perfusion After Initial Restoration of Postischemic Blood Flow. Circulation 80:1846–61 (1989). Neutrophils are believed to be important mediators of this phenomenon by accelerating vascular injury through the release of cytotoxic oxygen free radicals and proteolytic enzymes and by mechanically plugging capillary lumina. Engler, R. L., Schmid-Schoenbein, G. W., Pavelec, R. S.: Leukocyte Capillary Plugging in Myocardial Ischemia and Reperfusion in the Dog. Am. J. Pathol. 111:98–111 (1938). Fontone, J. C., Ward, P. A.: Polymorphonuclear Leukocyte-mediated Cell and Tissue Injury: Oxygen Metabolites and Their Relation to Human Disease. Human Pathol. 1 16:973–8 (1985). Wright, D. G., Gatlin, J. I.: Secretory Responses of Human Neutrophils: Exocytosis of Specific (secondary) Granules by Human Neutrophil During Adherence in Vitro and During Exudation in Vivo. J. Immunol. 123:285–96 (1970). We, therefore, postulated that the pharmacologic actions of adenosine which are mediated through the adenosine-2 receptor, such as vasodilatation, reduced neutrophil adherence to endothelial cells, inhibition of superoxide production from neutrophils and inhibition of platelet aggregation and thromboxane release, would most likely account for adenosine's protective effects against reperfusion injury. Cronstein, B. N., Levin, R. I., Belanoff, J., Weissman, G., Hirschron, R.: Adenosine: An Endogenous Inhibitor of Neutrophil-mediated Injury to Endothelial Cells. J. Clin. Invest. 78:760–70 (1986). Tanabe, M., Terashita, Z., Nishikawa, K., Hirata, M.: Inhibition of Coronary Circulatory Failure and Thromboxane $A_2$ Release During Coronary Occlusion and Reperfusion. J. Cardiovasc. Pharmacol. 6:442–8 (1984). Berne, R. M.: The Role of Adenosine in the Regulation of Coronary Blood Flow. Circ. Res. 47:807–13 (1980). Cronstein, B. N., Kramer, S. B., Weissman, G., Hirschorn, R.: Adenosine: A Physiologic Modulator of Superoxide Anion Generation by Human Neutrophils. J. Exp. Med. 158:1160–7 (1983).

The data presented in this application suggests that the protective effects of adenosine are not due to replenishment of the nucleotide pool but rather are mediated through activation of extracellular receptors. If the effects of adenosine were not receptor mediated, it is unlikely that $N^6$-cyclopentyladenosine and 2-[p-(2-carboxyethyl)phenethylamino]-5'-N-ethylcarbox amido adenosine), two metabolically inactive adenosine analogues, would be effective. It is interesting that infusions of either a selective adenosine-1 receptor or adenosine-2 receptor agonist reduce infarct size as much as adenosine. One interpretation of this finding is that activation of either of the adenosine receptor subtypes confers full protection and that activation of both receptor subtypes simultaneously provides no additional benefit compared to activation of each separately. Another possibility is that local concentrations of agonists at the site of infusion may be extremely high so that selectivity of $N^6$-cyclopentyladenosine and 2-[p-(2-carboxyethyl) phenethylamino]-540 -N-ethylcarboxamido adenosine) for their respective receptor subtypes on formed elements in the blood is lost. That is to say, it is possible, indeed likely, that formed elements, such as platelets and neutrophils, are exposed briefly to high levels of agonists as they pass by the tip of the infusion catheter. Thus, although $N^6$-cyclopentyladenosine is 1000-fold selective for the adenosine-1 receptor and 2-[p-(2-carboxyethyl)-phenethylamino]-5'-N-ethylcarbox amido adenosine) is at least 100-fold selective for the adenosine-2 receptor, all selectivity of both agonists may well be lost in the immediate vicinity of the infusion site. Hutchinson, A. J., Webb, R. L., Oei, H. H., Ghai, G., Zimmerman, M. B., Williams, M.: 2-[p-(2-carboxyethyl)phenethylamino]-5'-N-ethylcarbox amido adenosine), An adenosine-2 Selective Adenosine Receptor Agonist with Preferential Hypotensive Activity. J. Pharmacol.

and Exp. Ther. 251:47–55 (1989). Lohse, M. J., Klotz, K. N., Schwabe, L. L., Cristalli, G., Vittori, S., Grifantini, M.: 2-chloro-n6-cyclopentyladenosine: A Highly Selective Agonist at $A_1$ Adenosine Receptors. Naunyn-Schmiedeberg's Archives of Pharmacology. 337:697–689 (1988). If the agonist-induced biochemical changes in formed elements occur rapidly and are sustained after the agonists leave their receptors, and if the protective effects of adenosine agonists are mediated via adenosine receptors on formed elements, then both $N^6$-cyclopentyladenosine and 2-[p-(2-carboxyethyl)-phenethylamino]-5'-N-lethylcarbox amido adenosine) would be fully effective regardless of which receptor subtypes mediates the biochemical changes on the circulating formed elements. This hypothesis could also explain the fact that remarkably small doses of adenosine are fully effective in protecting against reperfusion injury.

The findings disclosed in this application relate to the treatment of patients with acute myocardial infarction. Administration of high doses of adenosine are not clinically tolerated in man since adenosine-2 receptor stimulation results in numerous intolerable side effects. These findings suggest that the administration of a nonhypotensive dose of an adenosine-1 receptor agonist, adenosine-2 receptor agonist and adenosine significantly attenuates myocardial reperfusion injury in the rabbit model.

The route of administration of the compounds is preferably intravenously but intracoranary or oral administration of suitable formulated compounds may also be utilized. The dose is generally given during the early period of reperfusion, but the compound can be administered just prior to reperfusion up to about 24 hours after reperfusion. It was found that nonhypotensive doses of adenosine or adenosine-2 receptor activating compound still protected the heart muscle, but did not cause negative side effects.

The preferred dose of adenosine and the adenosine-2 agonist ranges from about 0.3 μg/kg/min to 30 μg/kg/min. While the preferred dose of the adenosine-1 agonist ranges from about 0.03 μg/kg/min to 3 μg/kg/min. The broad range contemplated by this invention varies according to the route of administration, but can range up to about 300 μg/kg/min for adenosine and the adenosine-2 agonist and up to about 30 μg/kg/min for adenosine-1 agonist. It is understood that even lower doses than set out in the preferred range may in fact provide beneficial results. Compounds useful in this invention include the adenosine-2 receptor agonist 2-[p-(2-carboxyethyl)phenethylamino]-5'-N-ethylcarbox amido adenosine) and the adenosine-1 receptor agonist is cyclopentyl- adenosine.

The adenosine receptor agonists that are contemplated by this invention are those that are highly selective for a particular receptor; that is, a selective agonist is one that has a selectivity ratio of 100:1 for one receptor over another.

The pharmaceutically carrier includes any physiological saline, such as normal saline.

The following detailed example will further illustrate the invention although it will be understood that the invention is not limited to these specific examples.

EXAMPLE 1

Materials

Adenosine was obtained from Sigma Chemical, St. Louis, Mo. 2-[p-(2-carboxyethyl) phenethylamino]-5'-N-ethylcarboxamido adenosine) was synthesized in the Drug Discovery Division of Ciba-Geigy, Summit, N.J., and provided as a gift. Cyclopentyladenosine (CPA) was purchased from Research Biochemicals Inc. (Natick, N.J.).

Experiment preparation

New Zealand male white rabbits weighing 3–4 kg were utilized. Animals were anesthetized with intravenous sodium pentobarbital (initial dose of 45 mg) followed by 10 mg boluses until adequate anesthesia was obtained. Tracheotomy was performed and animals were ventilated with a Harvard positive pressure respirator throughout the experiment. Additional sodium pentobarbital was given as needed to maintain anesthesia during the procedure. Utilizing aseptic techniques, a femoral artery and vein were cannulated for measuring arterial blood pressure and for drug infusions, respectively. A left thoracotomy was performed at the fourth intercostal space, and the pericardium was incised and the left obtuse marginal branch of the circumflex artery was identified. A 4–0 silk ligature was placed around the artery just proximal to its branching near the atrial appendage, and the ends of the ligature were then enclosed in a polyethylene tubing (PE90). Arterial occlusion was achieved by pressing the tubing against the ventricular wall.

Experimental protocol

Prior to initiating the protocol, animals were randomly assigned to one of 11 treatment groups: 1) saline infusion only (control group)+lidocaine; 2) low dose adenosine (0.001 mg/min)+lidocaine; 3) intermediate dose adenosine (0.01 mg/min)+lidocaine; 4) high dose adenosine (0.1 mg/min)+lidocaine; 5) high dose adenosine without lidocaine; 6) low dose $N^6$-cyclopentyladenosine (a selective adenosine-1 receptor agonist; 0.0001 mg/min)+lidocaine; 7) intermediate dose $N^6$-cyclopentyladenosine (0.001 mg/min)+lidocaine; 8) high dose $N^6$-cyclopentyladenosine (0.01 mg/min)-+lidocaine; 9) low dose 2-[p-(2-carboxyethyl) phenethylamino]-5'-N-ethylcarboxamido adenosine) (a selective adenosine-2 receptor agonist; 0.001 mg/min) lidocaine; 10) intermediate dose 2-[p-(2-carboxyethyl)-phenethylamino]-5'-N-ethylcarbox amido adenosine) (0.01 mg/min)+lidocaine; and 11) high dose 2-[p-(2-carboxyethyl)phenethylamino]-5'-N-ethylcarboxamido adenosine) (0.1 mg/min)+lidocaine.

One electrocardiographic lead (lead 2 or 3) was monitored continuously throughout the protocol (Electronics for Medicine, Model VR-12). After the animals had been allowed to stabilize, baseline hemodynamic measurements were obtained. The animals then underwent 30 minutes of temporary occlusion. Occlusion of the vessel was confirmed by the appearance of epicardial cyanosis and ST segment elevation. Lidocaine (20 mg/ml) was administered during the first 15 minutes of occlusion to all groups except one of the groups receiving high dose adenosine. A 0.5 ml bolus was given approximately every four minutes for a total dose of 40 mg. Hemodynamic parameters were measured serially throughout the protocol. In the treatment groups, the various doses of adenosine or adenosine agonists were diluted in 0.9% NaCl and infused into the femoral vein utilizing a Braintree infusion pump. Infusions commenced five minutes prior to reperfusion and continued for the first 60 minutes of reperfusion at 12 ml/hr (total volume=13 ml). The control group received an equivalent volume of saline. Reperfusion of the vessel was achieved by release of the ligature. Successful reperfusion was confirmed by visualization of arterial blood flow through the artery, disappearance of epicardial cyanosis, and rapid resolution of ST segment changes. After one hour of reperfusion, the loose ligature was secured and the chest and tracheotomy closed.

After 48 hours of reperfusion the animals were reanesthetized with 50 mg of sodium pentobarbital and reintubated through a tracheotomy. The thoracotomy site was reopened and the ligature was tightened. Monastral blue (1 ml/kg) was administered via the marginal ear vein over one minute to define the area at risk. The heart was rapidly removed from the chest, washed to prevent counterstaining, and fixed in 10% phosphate buffer formaldehyde.

Analysis of area at risk and area of infarction

The heart was sectioned in 4-5 slices at 3-4 mm intervals parallel to the posterior atrioventricular groove and photographed for later confirmation of area at risk. The right ventricle was removed and the left ventricular slices weighed. Tissue sections were then dehydrated and embedded in paraffin. Microscopic sections (4μ) were cut and stained with hematoxylin-eosin and Masson's trichrome stain. The paraffin blocks were superimposed on the histologic sections on glass slides and the area at risk (AR) marked. This was further confirmed from the gross photographs. The area at risk (AR) and the area of necrosis (AN) (stained grey by trichrome stain) were enlarged (10X) using a microscopic projector and quantitated by computerized planimetry. The extent of left ventricular necrosis and risk region were computed using the total area and weight of the left ventricle as previously described by an observer unaware of the treatment groups. Virmani, R., Kolodgie, F. D., Osmilowski, A., Forman, M. B.: Effect of Perfluorochemical Fluosol-DA on Myocardial Infarct Healing in the Rabbit. AM. J. Cardiovasc. Path. 69-80 (1990).

Statistical analysis

All data are express as mean ± standard error of the mean. For each parameter, the 11 groups were compared by a 1-factor analysis of variance. If this analysis indicated significant differences among the group means, the control group was compared to each of the treatment groups using a Fisher's LSD test. Complex null hypotheses involving several groups were tested with specific contrasts using the appropriate contrast coefficients. Statistical analyses were conducted on an IBM-compatible PC using the Number Crunchers Statistical System (Kaysville, Utah), and the criterion of significance was $P \leq 0.05$.

RESULTS

Exclusion criteria were established prior to commencing the study. These included ventricular tachycardia or fibrillation persisting for greater than two minutes, absence of a definable area at risk, and failure to survive for 48 hours after reperfusion. Data from 86 rabbits were included in the final analysis. Eight controls, 8 high dose adenosine without lidocaine, 7 high dose adenosine with lidocaine, 8 intermediate dose adenosine, 7 low dose adenosine, 9 high dose 2-[p-(2-carboxyethyl)phenethylamino]-5'-N-ethylcarbox amido adenosine), 8 intermediate dose 2-[p-(2-carboxyethyl)-phenethylamino]-5'-N-ethylcarbox amido adenosine), 7 low dose 2-[p-(2-carboxyethyl)phenethylamino]-5'-N-ethylcarbox amido adenosine), 8 high dose $N^6$-cyclopentyladenosine, 8 intermediate dose $N^6$-cyclopentyladenosine, and 8 low dose $N^6$-cyclopentyladenosine.

Hemodynamic parameters (Table I)

None of the doses of adenosine or the low and intermediate doses of 2-[p-(2-carboxyethyl)phenethylamino]-5'-N-ethylcarbox amido adenosine) altered heart rate, systolic, diastolic, or mean arterial blood pressure, or the rate-pressure product, an indirect measure of myocardial oxygen consumption. However, cyclopentyladenosine, the adenosine-1 receptor agonist, produced significant bradycardia and hypotension during infusion of the highest dose.

TABLE 1-A

Hemodynamic Parameters During Experimental Protocol

| | HEART RATE (beats/minutes) | | | | | SYSTOLIC BLOOD PRESSURE (mmHg) | | | | |
|---|---|---|---|---|---|---|---|---|---|---|
| | Base | OCC | Rep | R-15 | R-45 | Base | OCC | Rep | R-15 | R-45 |
| CONTROL | 265 ± 10 | 248 ± 9 | 231 ± 11 | 230 ± 10 | 231 ± 8 | 114 ± 4 | 99 ± 7 | 95 ± 5 | 92 ± 5 | 100 ± 5 |
| *ADO-High/Lido | 248 ± 10 | 243 ± 9 | 237 ± 11 | 237 ± 10 | 244 ± 8 | 107 ± 4 | 94 ± 6 | 98 ± 5 | 95 ± 5 | 100 ± 5 |
| ADO-Low | 242 ± 10 | 239 ± 10 | 223 ± 12 | 224 ± 10 | 229 ± 9 | 111 ± 5 | 98 ± 7 | 101 ± 6 | 102 ± 6 | 110 ± 5 |
| ADO-Int | 254 ± 10 | 244 ± 9 | 228 ± 11 | 226 ± 10 | 236 ± 8 | 118 ± 4 | 95 ± 6 | 93 ± 6 | 93 ± 6 | 106 ± 5 |
| ADO-High | 261 ± 10 | 250 ± 10 | 230 ± 12 | 226 ± 10 | 231 ± 9 | 122 ± 5 | 101 ± 7 | 106 ± 6 | 100 ± 6 | 104 ± 5 |
| CPA-Low | 238 ± 10 | 216 ± 9 | 219 ± 11 | 213 ± 10 | 216 ± 8 | 108 ± 4 | 94 ± 6 | 98 ± 5 | 95 ± 5 | 105 ± 5 |
| CPA-Int | 249 ± 10 | 224 ± 9 | *191 ± 11 | *173 ± 10 | *171 ± 8 | 118 ± 4 | 100 ± 7 | 101 ± 5 | 88 ± 5 | 95 ± 5 |
| CPA-High | 251 ± 10 | 234 ± 9 | *176 ± 11 | *151 ± 10 | *138 ± 8 | 107 ± 4 | 92 ± 6 | 86 ± 5 | 78 ± 5 | *80 ± 5 |
| CGS-Low | 257 ± 10 | 240 ± 11 | 225 ± 12 | 224 ± 10 | 230 ± 9 | 121 ± 5 | 97 ± 7 | 104 ± 6 | 100 ± 6 | 102 ± 6 |
| CGS-Int | 243 ± 10 | 227 ± 9 | 222 ± 11 | 222 ± 10 | 229 ± 8 | 113 ± 4 | 90 ± 6 | 94 ± 5 | 88 ± 5 | 95 ± 5 |
| CGS-High | 256 ± 10 | 249 ± 9 | 239 ± 11 | 254 ± 10 | 251 ± 8 | 117 ± 4 | 102 ± 6 | 91 ± 5 | 82 ± 56 | *76 ± 6 |

*ADO-High/Lido = high dose adenosine without lidocaine; ADO-Low, ADO-Int, ADO-High = low, intermediate and high dose of adenosine; Base = base line; CGS-Low, CGS-Int, CGS-High = low, intermediate, and high dose of CGS 21680C = (2-[p-(2-carboxyethyl)phenthylamino]-5¹-N-ethylcarboxamido adenosine); CPA-Low, CPA-Int, CPA-High = low, intermediate, and high dose of cyclopentyladenosine; OCC = 25 minutes into occlusion; Rep = immediately reperfusion; R-15 = 15 minutes after reperfusion; R-45 = 45 minutes after reperfusion.

TABLE 1-B

Hemodynamic Parameters During Experimental Protocol

TABLE 1-B-continued

| | DIASTOLIC BLOOD PRESSURE (mmHg) | | | | | MEAN BLOOD PRESSURE (mmHg) | | | | |
|---|---|---|---|---|---|---|---|---|---|---|
| | Base | OCC | Rep | R-15 | R-45 | Base | OCC | Rep | R-15 | R-45 |
| CONTROL | 77 ± 4 | 74 ± 5 | 67 ± 4 | 62 ± 4 | 67 ± 4 | 89 ± 4 | 80 ± 6 | 75 ± 5 | 72 ± 4 | 78 ± 4 |
| *ADO-High/Lido | 73 ± 4 | 66 ± 5 | 67 ± 4 | 67 ± 4 | 72 ± 3 | 85 ± 4 | 76 ± 5 | 77 ± 5 | 76 ± 4 | 82 ± 4 |
| ADO-Low | 71 ± 4 | 65 ± 5 | 67 ± 4 | 67 ± 4 | 72 ± 4 | 84 ± 4 | 76 ± 6 | 78 ± 5 | 79 ± 5 | 84 ± 4 |
| ADO-Int | 79 ± 4 | 65 ± 5 | 63 ± 4 | 64 ± 4 | 71 ± 3 | 88 ± 4 | 74 ± 5 | 72 ± 5 | 72 ± 5 | 83 ± 4 |
| ADO-High | 78 ± 4 | 66 ± 5 | 69 ± 4 | 65 ± 4 | 64 ± 4 | 93 ± 4 | 78 ± 6 | 77 ± 5 | 75 ± 5 | 77 ± 4 |
| CPA-Low | 72 ± 4 | 62 ± 5 | 65 ± 4 | 61 ± 4 | 64 ± 4 | 84 ± 4 | 72 ± 5 | 76 ± 5 | 72 ± 4 | 76 ± 4 |
| CPA-Int | 80 ± 4 | 65 ± 5 | 64 ± 4 | 54 ± 4 | 56 ± 3 | 89 ± 4 | 77 ± 6 | 76 ± 5 | 65 ± 4 | 69 ± 4 |
| CPA-High | 70 ± 4 | 62 ± 5 | 55 ± 4 | *47 ± 4 | *44 ± 3 | 82 ± 4 | 72 ± 5 | 65 ± 5 | *57 ± 4 | *56 ± 4 |
| CGS-Low | 80 ± 4 | 65 ± 6 | 63 ± 4 | 68 ± 4 | 65 ± 4 | 94 ± 4 | 76 ± 6 | 75 ± 5 | 74 ± 5 | 77 ± 4 |
| CGS-Int | 75 ± 4 | 61 ± 5 | 63 ± 4 | 54 ± 4 | 57 ± 3 | 88 ± 4 | 71 ± 5 | 73 ± 5 | 65 ± 4 | 70 ± 4 |
| CGS-High | 81 ± 4 | 72 ± 5 | 57 ± 4 | 52 ± 4 | *46 ± 3 | 93 ± 4 | 82 ± 5 | 68 ± 5 | 62 ± 5 | *56 ± 4 |

| | RATE PRESSURE PRODUCT (HR × SBP) / 1000 | | | | |
|---|---|---|---|---|---|
| | Base | OCC | Rep | R-15 | R-45 |
| CONTROL | 30.2 ± 2 | 25.3 ± 2 | 22.2 ± 2 | 21.2 ± 2 | 22.5 ± 2 |
| *ADO-High/Lido | 26.6 ± 2 | 22.9 ± 2 | 23.3 ± 2 | 22.5 ± 2 | 24.8 ± 2 |
| ADO-Low | 28.4 ± 2 | 23.5 ± 2 | 22.6 ± 2 | 23.1 ± 2 | 25.1 ± 2 |
| ADO-Int | 30.0 ± 2 | 23.3 ± 2 | 21.0 ± 2 | 20.8 ± 2 | 24.0 ± 2 |
| ADO-High | 31.8 ± 2 | 25.5 ± 2 | 24.6 ± 2 | 22.9 ± 2 | 24.3 ± 2 |
| CPA-Low | 26.1 ± 2 | 21.5 ± 2 | 22.0 ± 2 | 20.4 ± 2 | 22.0 ± 2 |
| CPA-Int | 29.4 ± 2 | 22.6 ± 2 | 19.6 ± 2 | 15.3 ± 2 | 16.3 ± 2 |
| CPA-High | 26.9 ± 2 | 21.5 ± 2 | 15.4 ± 2 | *12.0 ± 2 | *11.1 ± 2 |
| CGS-Low | 31.2 ± 2 | 26.1 ± 2 | 23.3 ± 2 | 22.6 ± 2 | 23.5 ± 2 |
| CGS-Int | 27.6 ± 2 | 20.7 ± 2 | 21.1 ± 2 | 19.7 ± 2 | 21.9 ± 2 |
| CGS-High | 30.0 ± 2 | 25.4 ± 2 | 22.3 ± 2 | 20.7 ± 2 | 19.6 ± 2 |

*ADO-High/Lido = high dose adenosine without lidocaine; ADO-Low, ADO-Int, ADO-High = low, intermediate and high dose of adenosine; Base = base line; CGS-Low, CGS-Int, CGS-High = low, intermediate, and high dose of CGS 21680C = (2-[p-(2-carboxyethyl)phenthylamino]-5$^1$-N-ethylcarboxamido adenosine); CPA-Low, CPA-Int, CPA-High = low, intermediate, and high dose of cyclopentyladenosine; HR = heart rate; OCC = 25 minutes into occlusion; Rep = immediately reperfusion; R-15 = 15 minutes after reperfusion; R-45 = 45 minutes after reperfusion; SBP = systolic blood pressure.

Figure 1:
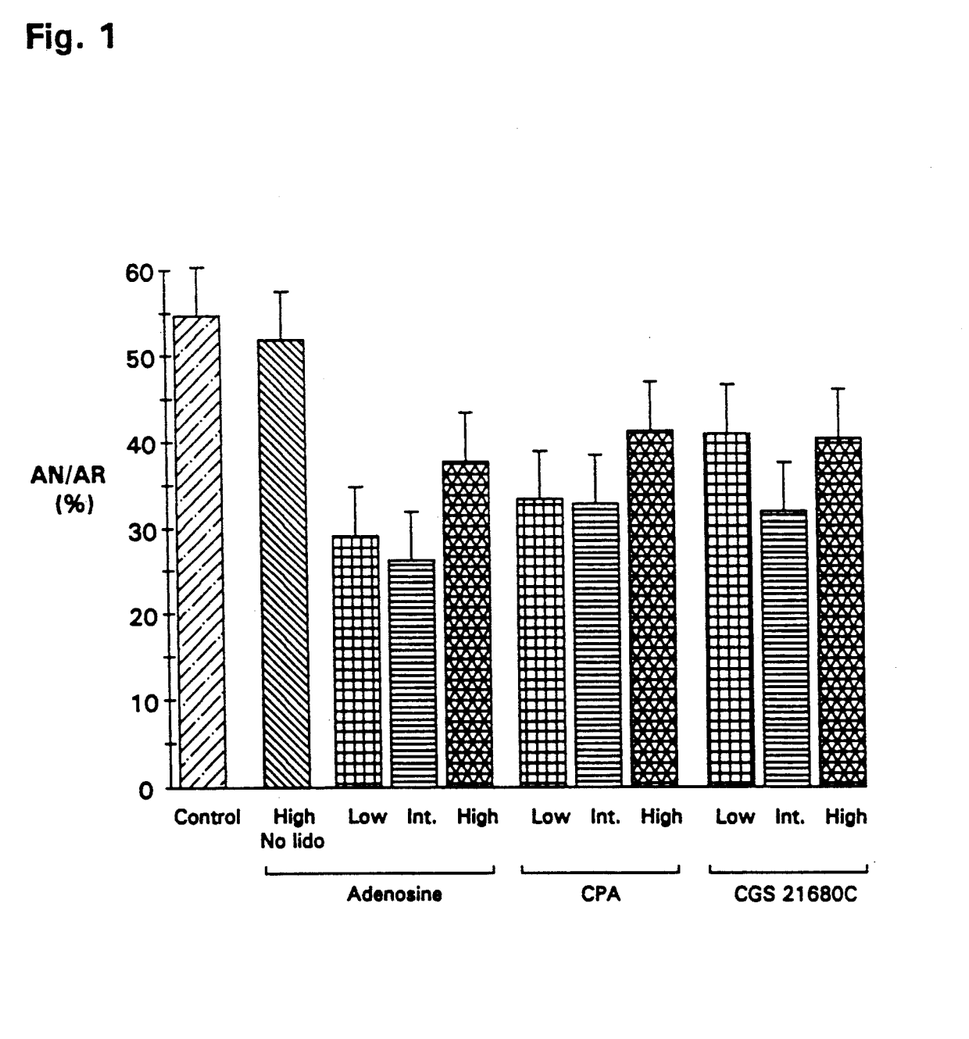
FIG. 1 shows change in infarct size verses a control for several compounds.

Infarct size (Table II, FIG. 1)

No significant differences in the area at risk, expressed as a percentage of the total left ventricle, were noted among the groups. Infarct size, expressed as a percentage of the area at risk, was similar in the control group and the high dose adenosine group without lidocaine (54.7±5.5% vs. 51.5±5.5±5.5%; NS). A significant reduction in infarct size was noted with all 3 doses of adenosine when compared to control (low: 29.2±5.8%; p=0.002, intermediate: 25.9±5.5; p<0.0004, high: 27.5±5.8; p=0.03). Both the intermediate and low doses of the adenosine-1 receptor agonist, N$^6$-cyclopentyladenosine, also significantly reduced infarct size, expressed as a percentage of the risk region when compared to control animals (low dose: 33.0±5.5%; p=0.006, intermediate dose: 32.5±5.5%; p=0.005). In contrast, the high dose of N$^6$-cyclopentyladenosine only resulted in moderate salvage that was nearly significant (40.8±5.5%; p=0.08). This was probably because the high dose of N$^6$-cyclopentyladenosine caused severed bradycardia and subsequent hypotension resulting in relative myocardial ischemia during the infusion. Infarct size reduction was also observed with both the intermediate and high doses of the adenosine-2 receptor agonist, 2-[p-(2-carboxyethyl)phenethylamino]-5'-N-ethylcarbox amido adenosine), when compared to control (intermediate: 31.6±5.5%; p=0.004, high: 39.8±5.1%; p=0.05) with a tendency for reduction with the low dose (40.5±5.8%; p=0.08). When the mean effect of all three doses of adenosine or either of the two selective agonists were compared to the control group (i.e., the null hypothesis was X$_{control}$=(X$_{low\ dose}$+X$_{intermediate\ dose}$+X$_{high\ dose}$/3), a highly signficant reduction in infarct size was observed (adenosine: 31.0±5.2%; p=0.994, cyclopentyladenosine : 25.0±5.1%; p=0.003, CGS 37.0 ±5.3%; p=0.007). No differences were observed when individual agonists were compared to one another, i.e., there was no significant difference in the protective effect of adenosine versus N$^6$-cyclopentyladenosine versus 2-[p-(2-carboxyethyl)phenethylamino]-5'-N-ethylcarbox amido adenosine). Also, the combined effect of both agonists was not significantly different from the adenosine group. [Null hypothesis: (X$_{low\ dose\ adenosine}$+X$_{intermediate\ dose\ adenosine}$+X$_{high\ dose\ adenosine}$)/3=(X$_{low\ dose\ cyclopentyladenosine}$+X$_{intermediate\ dose\ cyclopentyladenosine}$+X$_{high\ dose\ cyclopentyladenosine}$+X$_{low\ dose\ 2-[p-(2-carboxyethyl)phenethylamino]-5_1-N-ethylcarboxamido\ adenosine}$+X$_{intermediate\ dose\ 2-[p-(2-carboxyethyl)phenethylamino]-5_1-N-ethylcarboxamido\ adenosine}$+X$_{high\ dose\ 2-[p-(2-carboxyethyl)phenethylamino]-5_1-N-ethylcarboxamido\ adenosine}$))/6].

While the present invention has been described by reference to certain illustrative examples, various modifications and variants within the spirit and scope of the invention will be apparent to those skilled in the art.

TABLE 2

| Effect of Serial Doses of Adenosine and Selective A$_2$ and A$_1$ Agonists on Infarct Size | | | | | | | | |
|---|---|---|---|---|---|---|---|---|
| | Control | *High- no Lido | Adenosine | | | CPA | | |
| | | | Low | Int | High | Low | Int | High |
| AR/LV (%) | 51.1 ± 4.9 | 29.2 ± 4.9 | 46.1 ± 5.2 | 51.4 ± 4.9 | 46.9 ± 5.2 | 47.2 ± 4.9 | 54.4 ± 4.9 | 57.4 ± 4.9 |
| AN/AR (%) | 54.6 ± 5.5 | 51.5 ± 5.5 | 29.2 ± 5.8 | 25.9 ± 5.5 | 37.5 ± 5.8 | 33.0 ± 5.5 | 32.5 ± 5.5 | 40.8 ± 5.5 |
| AN/LV (%) | 29.3 ± 3.8 | 31.2 ± 3.8 | 13.8 ± 4.0 | 13.6 ± 3.8 | 18.1 ± 4.0 | 15.7 ± 3.8 | 16.7 ± 3.8 | 23.9 ± 3.8 |

CGS 21680C

TABLE 2-continued

|  | Low | Int | High |
|---|---|---|---|
| AR/LV (%) | 57.5 ± 5.2 | 59.1 ± 4.9 | 51.7 ± 4.6 |
| AN/AR (%) | 40.5 ± 5.8 | 31.6 ± 5.5 | 39.8 ± 5.1 |
| AN/LV (%) | 23.1 ± 4.0 | 18.5 ± 3.8 | 21.2 ± 3.5 |

AR = Area at Risk; AN = Area of Necrosis; LV = Left Ventricle; CGS 21680C = (2-[p-(2-carboxyethyl)phenethylamino]-$5^1$-N-ethylcarboxamido adenosine); CPA = Cyclopentyladenosine; *High-no Lido = high dose adenosine without prophylactic lidocaine; Int = intermediate dose; = p = 0.05 vs. control

We claim:

1. The method to reduce myocardial reperfusion injury in a patient without causing a hypotensive reaction comprising:
   A) coadministering between 0.03 μg/kg/min. to 30 μg/kg/min. of adenosine or an analogue thereof and an effective dose of lidocaine.

2. The method of claim 1 wherein said analogue is 2-[p-(2-carboxyethyl)phenethylamino]-5'-N-ethylcarboxamido adenosine.

3. The method of claim 2 wherein said analogue dosage ranges from 0.03 μg/kg/min. to 30 μg/kg/min.

4. The method of claim 1 wherein said analogue is $N^6$-cyclopentyladenosine.

5. The method to reduce myocardial reperfusion injury in a patient without causing a hypotensive reaction comprising:
   (a) coadministering between 0.03 μg/kg/min. to 3 μg/kg/min. of adenosine-1 receptor agonist and an effective dose of lidocaine.

6. The method of claim 5 wherein said adenosine-1 receptor agonist is $N^6$-cyclopentyladenosine.

7. The method to reduce myocardial reperfusion injury in a patient without causing a hypotensive reaction comprising:
   (a) coadministering between 0.03 μg/kg/min. to 30 μg/kg/min. of adenosine-2 receptor agonist and an effective dose of lidocaine.

8. The method of claim 6 wherein said adenosine-2 receptor agonist is 2-[p-(2-carboxyethyl)phenethylamino]-5'-N-ethylcarboxamido adenosine.

* * * * *

UNITED STATES PATENT AND TRADEMARK OFFICE
CERTIFICATE OF CORRECTION

PATENT NO. : 5,206,222
DATED : Apr. 27, 1993
INVENTOR(S) : Forman et al.

It is certified that error appears in the above-indentified patent and that said Letters Patent is hereby corrected as shown below:

Column 3, line 10 delete "$^9F$" and insert --$^{19}F$--.
Column 4, line 52 delete "540" and insert --5'--.
Column 5, line 12 delete "lethylcarbox" and insert --ethylcarbox-
Column 10, line 52, delet "$5_1$" and insert --5'--; line 53 delete "$5_1$" and insert --5'--; line 54 delete "$5_1$" and insert --5'--.
Column 12, line 20, delete "0.03" and insert --0.3--

Signed and Sealed this

Twenty-fifth Day of April, 1995

Attest:

BRUCE LEHMAN

Attesting Officer     Commissioner of Patents and Trademarks